(12) United States Patent
Sinha et al.

(10) Patent No.: US 11,178,389 B2
(45) Date of Patent: Nov. 16, 2021

(54) SELF-CALIBRATING DISPLAY DEVICE

(71) Applicant: Microsoft Technology Licensing, LLC, Redmond, WA (US)

(72) Inventors: Praveen Sinha, Hyderabad (IN); Seema Lal Gulabrani, Hyderabad (IN); Ajay Vellanki, Hyderabad (IN); Rahul Agarwal, Hyderabad (IN); Arun Mudiraj, Hyderabad (IN)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 16/363,854

(22) Filed: Mar. 25, 2019

(65) Prior Publication Data

US 2020/0314416 A1 Oct. 1, 2020

(51) Int. Cl.
*H04N 13/327* (2018.01)
*G06F 3/01* (2006.01)
(Continued)

(52) U.S. Cl.
CPC ........... *H04N 13/327* (2018.05); *G06F 3/013* (2013.01); *G06F 3/04847* (2013.01);
(Continued)

(58) Field of Classification Search
CPC .............. G02B 27/017; G02B 27/0172; G02B 27/0176; G02B 27/0093; G02B 2027/0132–0136; G02B 2027/0174; G02B 2027/0178; G06F 3/012; G06F 3/013; H04N 5/7491; H04N 13/327;
(Continued)

(56) References Cited

U.S. PATENT DOCUMENTS 7,744,216 B1 6/2010 Uhlhorn
2013/0002722 A1 1/2013 Krimon et al.
(Continued)

OTHER PUBLICATIONS

"Accommodation (eye)", Retrieved from: https://en.wikipedia.org/wiki/Accommodation_(eye), Feb. 18, 2018, 4 Pages.
(Continued)

*Primary Examiner* — Priyank J Shah
(74) *Attorney, Agent, or Firm* — Fiala & Weaver P.L.L.C.

(57) ABSTRACT

A system is described for automatically calibrating a display device based at least on information relating to a user of the display device. The system obtains visual acuity information or pupillary information of the user. The system then determines a value of a display parameter of the display device based at least on the visual acuity information or the pupillary information of the user. The determined value is then provided for application to the display device. Other information may also be used in determining the value of the display parameter, such as user input, demographic information of the user, display device specific information, user environment information, displayed content information, or application context information. An algorithm may be used that determines the display parameter based on such information. The algorithm may comprise a model obtained through machine learning.

22 Claims, 9 Drawing Sheets

US 11,178,389 B2

Page 2

(51) Int. Cl.
    *G06F 3/0484*     (2013.01)
    *G09G 3/20*     (2006.01)

(52) U.S. Cl.
    CPC ... *G09G 3/2088* (2013.01); *G09G 2320/0626* (2013.01); *G09G 2320/0693* (2013.01)

(58) Field of Classification Search
    CPC ..... G09G 2320/0626; G09G 2320/066; G09G 2320/0693
    See application file for complete search history.

(56) References Cited

U.S. PATENT DOCUMENTS

| | | | |
|---|---|---|---|
| 2014/0282646 A1 | 9/2014 | Mccoy et al. | |
| 2015/0310287 A1* | 10/2015 | Tseng | G06K 9/0061 382/104 |
| 2016/0266643 A1 | 9/2016 | Martensson et al. | |
| 2016/0270656 A1* | 9/2016 | Samec | A61B 3/1241 |
| 2016/0334868 A1* | 11/2016 | Pacheco | G06F 3/013 |
| 2017/0263192 A1 | 9/2017 | Luna et al. | |
| 2017/0293146 A1* | 10/2017 | Nicholls | G02B 27/0172 |
| 2018/0211608 A1 | 7/2018 | Reddy et al. | |
| 2018/0308252 A1 | 10/2018 | Alonso | |
| 2019/0094552 A1* | 3/2019 | Shousha | A61B 3/113 |
| 2020/0124845 A1* | 4/2020 | Smith | G06F 3/14 |

OTHER PUBLICATIONS

"Are pupil size calculations possible with Tobii Eye Trackers?", Retrieved from: https://www.tobiipro.com/learn-and-support/learn/eye-tracking-essentials/is-pupil-size-calculations-possible-with-tobii-eye-trackers/, Sep. 26, 2016, 2 Pages.
"Astigmatism", Retrieved from: http:/www.vision-and-eye-health.com/astigmatism.html, Oct. 16, 2011, 3 Pages.
"Defect of Vision", Retrieved from: https://cbsescience.in/2007/01/02/defects-of-vision-and-their-correction/, Jan. 2, 2007, 53 Pages.
"Defects of the Eye", Retrieved from: http://www.chm.bris.ac.uk/webprojects2002/upton/defects_of_the_eye.htm, Jan. 27, 2014, 2 Pages.
"Digital Eye Strain", Retrieved from: https://www.thevisioncouncil.org/content/digital-eye-strain, Sep. 25, 2015, 3 Pages.
Zuva, Patrick, "4 best eye tracking laptops to own in 2019", Retrieved from: https://windowsreport.com/eye-tracking-laptops/, Jan. 29, 2019, 27 Pages.
"Eye Disorder / Refractive Disorder", Retrieved from: http:/www.lenzomem.com/EyeDisorders, Jan. 10, 2016, 3 Pages.
"Eye tracking", Retrieved from: http:/en.wikipedia.org/wiki/Eye_tracking, Mar. 3, 2014, 13 Pages.
"Eye tracking for research", Retrieved from: http://www.tobii.com/en/eye-tracking-research/global/library/white-papers/tobii-eye-tracking-white-paper/#.UuqPpBCSwwA, Retrieved Date: Jan. 31, 2019, 6 Pages.
"Fujitsu Develops Eye Tracking Technology", Retrieved from: http://www.fujitsu.com/global/about/resources/news/press-releases/2012/1002-02 html, Oct. 2, 2012, 4 Pages.
"GP3 Eye Tracker | Hardware Only", Retrieved from: http:/www.gazept.com/product/gazepoint-gp3-eye-tracker/#Lightbox/0, Jun. 6, 2017, 5 Pages.
"How The Eye Focuses Light", Retrieved from: http://www.sciencelearn.org.nz/Contexts/Light-and-Sight/Science-Ideas-and-Concepts/How-the-eye-focuses-light, Apr. 18, 2012, 6 Pages.
"How The Eyes Work", Retrieved from: https://web.archive.org/web/20021120092119/http://www.jsei.org/patient_care/home_eyeworks.htm, Nov. 20, 2002, 1 Page.

"Lasik Eye Center", Retrieved from: http://lasikeyecenter.blogspot.in/2009/01/hyperopia-hypermetropia.html, Retrieved Date: Jan. 2009, 2 Pages.
"Millimetre", Retrieved from: http:/en.wikipedia.org/wiki/Millimetre, Dec. 30, 2016, 2 Pages.
Tang, Melvin, "5 ways to ruin your eyesight", Retrieved from: https://www.stuff.tv/my/features/5-ways-ruin-your-eyesight, Mar. 6, 2014, 6 Pages.
"Optics and Vision", Retrieved from: http:/en.wikipedia.org/wiki/Optics_and_vision, Aug. 12, 2012, 4 Pages.
"Presbyopia", Retrieved from: https:/www.nei.nih.gov/healthyeyes/presbyopia, Jan. 5, 2015, 4 Pages.
"Survey of Users with Low Vision Results", Retrieved from: https://webaim.org/projects/lowvisionsurvey/#proficiency, Mar. 2013, 11 Pages.
"Television Watching Statistics", Retrieved from: http://www.statisticbrain.com/television-watching-statistics/, May 23, 2017, 9 Pages.
"Tobii Pro Nano", Retrieved from: https://www.tobiipro.com/product-listing/nano/, Retrieved Date: Jan. 31, 2019, 11 Pages.
"Tobii Pro Spectrum", Retrieved from: https:/www.tobiipro.com/product-listing/tobii-pro-spectrum/, Nov. 13, 2016, 13 Pages.
"Treatment for Astigmatism", Retrieved from: http://healthlob.com/2011/05/treatment-astigmatism/, May 6, 2011, 2 Pages.
Baris, Toprak A.., "File:Myopia.svg", Retrieved from: http://en.wikipedia.org/wiki/File:Myopia.svg, Mar. 27, 2007, 4 Pages.
Dahl, Jeff, "File:Snellen chart.svg", Retrieved from: https://en.wikipedia.org/wiki/File:Snellen_chart.svg, Jul. 23, 2008, 5 Pages.
Dean, Jeremy, "10 Messages My Pupils Are Sending You", Retrieved from: https://www.spring.org.uk/2011/12/what-the-eyes-reveal-10-messages-my-pupils-are-sending-you.php, Dec. 15, 2011, 12 Pages.
Herman, Snellen, "Snellen Chart", Retrieved from: https://en.wikipedia.org/wiki/Snellen_chart, Dec. 17, 2004, 2 Pages.
Kaszubski, Debra, "Electronic devices may be linked to nearsightedness", Retrieved from: https://www.theoaklandpress.com/lifestyles/electronic-devices-may-be-linked-to-nearsightedness/article_39f9f517-6730-50d8-976b-64bbbf7137d1.html. May 8, 2018, 3 Pages.
Ker, Than, "How the Human Eye Works", Retrieved from: https://www.livescience.com/3919-human-eye-works.html, May 5, 2016, 5 Pages.
Lacey, Martha DE., "British people spend Nine Hours a day (that's 30 Years of our Lives) staring at screens . . . and more time online than Any other nation in the world". Retrieved from: http://www.dailymail.co.uk/femail/article-2256067/British-people-spend-NINE-HOURS-day-staring-screens-time-internet-ANY-nation-say-NetVoucherCodes.html, Jan. 2, 2013, 39 Pages.
McDonough, Megan, "Sideways Eye-Tracking Prototype Sees What You're Ogling While Shopping", Retrieved from: https://www.digitaltrends.com/computing/sideways-eye-tracking-prototype-sees-what-youre-ogling-while-shopping/, Apr. 29, 2013, 11 Pages.
Miller, Thomas, "How much time do you spend using a computer?", Retrieved from: https://www.quora.com/How-much-time-do-you-spend-using-a-computer, Feb. 15, 2018, 3 Pages.
Penzo, Matteo, "Introduction To Eyetracking: Seeing Through User's Eye", Retrieved from: https://www.uxmatters.com/mt/archives/2005/12/introduction-to-eyetracking-seeing-through-your-users-eyes.php, Dec. 6, 2005, 10 Pages.
Peter, Svensson, "New Eye Tracking Laptop Leaves the Lab", Retrieved from: https://web.archive.org/web/20110304185201/http:/www.huffingtonpost.com/2011/03/01/eye-tracking-feature-laptops_n_829614.html, Jan. 3, 2011, 3 Pages.
Poock, Gary K., "Information Processing vs Pupil Diameter", In Journal of Perceptual and Motor Skills: vol. 37, Issue 3, Dec. 1, 1973, Abstract.
"International Search Report and Written Opinion Issued in PCT Application No. PCT/US20/015762", dated Apr. 24, 2020, 16 Pages.

* cited by examiner

300

Display Parameters

- Screen Contrast, Screen Brightness, Screen Resolution, Screen Orientation
- Font Size, Font Effect, Font Orientation
- Color temperature, color profile/filter application

900

| Features Utilized by Machine Learner and Model |
|---|
| • Visual acuity information for a user
• Pupillary information for a user
• User input
• Demographic information for the user (e.g., age, gender, ethnicity, location, vision correction requirement, reading comprehension level, etc.)
• Display device specific information
• User environment information
• Display content information
• Application context information |

FIG. 9

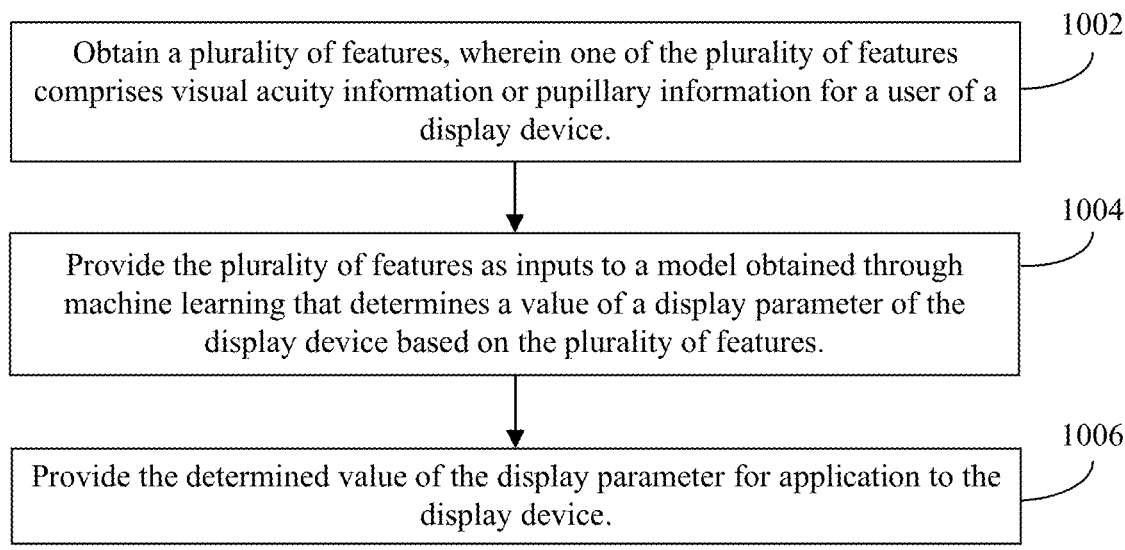

FIG. 10

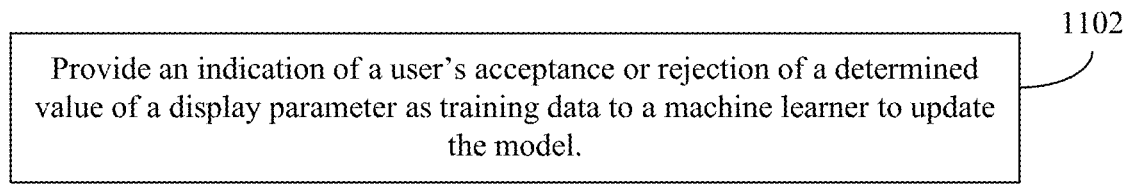

FIG. 11

SELF-CALIBRATING DISPLAY DEVICE

BACKGROUND

In our modern lifestyle, a large amount of time is spent using electronic devices with display screens, such as laptops, desktops, electronic readers, smartphones, and televisions. On average, a person may be looking at a digital screen for up to 15 hours a day. The heavy use of mobile phones has recently increased in a sudden manner, as compared to a decade earlier. The extensive use of electronic devices adversely affects the eyes of the users of the devices. The impact may be abrupt or gradual, based on other supplemental factors, such as age and eye health of the user. A large percentage of computer users has a visual limitation of some form and needs prescription glasses. Some researchers predict that by 2050 half of the world's population will be nearsighted (myopic) due to continuous focus on their electronic devices. If the visual limitation of myopia is not treated properly, it could lead to the complete loss of eyesight.

In addition, studies have shown that the extended viewing of the digital screen creates strain on the muscles of the eyes, causing health problems such as headaches, dry or watery eyes, or concentration issues. Regular and continuous straining of the eye muscles can inhibit smooth functioning of these muscles and may cause vision defects. These muscles are responsible for changing the size of the pupil in response to light and other visual and emotional stimuli. For instance, when under stress, the pupils of a person can become constricted, leading to difficulty in reading or working. In contrast, the emotional response from viewing a flag of one's own country may cause dilation of the pupils.

For persons with normal eyesight, the prolonged usage of digital displays may cause eye discomfort and vision problems or computer vision syndrome. For persons already suffering from visual limitations, the problem is compounded with newer defects in addition to existing ones. The current solutions for eye strain issues and other vision problems include prescription glasses or contact lenses, which come with an attendant set of problems, for example, straining of the ears and noses, maintenance needs, and eye redness or dryness. Moreover, the prescription glasses or contact lenses are permanent correction methods that do not change with pupil dilation fluctuations.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

A system is described herein for automatically calibrating a display device based at least on information relating to a user of the display device. The system obtains visual acuity information or pupillary information of the user. The system then determines a value of a display parameter of the display device based at least on the visual acuity information or the pupillary information of the user. The determined value may be provided for application to the display device. In certain implementations, information other than visual acuity or pupillary may also be used in determining the value of the display parameter, such as user input, demographic information of the user, display device specific information, user environment information, displayed content information, or application context information. In other aspects, an algorithm may be used that determines the display parameter based on such information. The algorithm may comprise a model obtained through machine learning.

Further features and advantages of various embodiments, as well as the structure and operation of the various embodiments, are described in detail below with reference to the accompanying drawings. It is noted that the embodiments are not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate embodiments of the present application and, together with the description, further serve to explain the principles of the embodiments and to enable a person skilled in the pertinent art to make and use the embodiments.

FIG. 9 depicts a list of features that may be used by a machine learner and a model for determining display device settings, according to an example embodiment.

FIG. 10 depicts a flowchart of a method for calibrating a display device using a model obtained through machine learning, according to another example embodiment.

FIG. 11 depicts a flowchart of a method for providing information as training data to a machine learner, according to an example embodiment.

Figure 1:
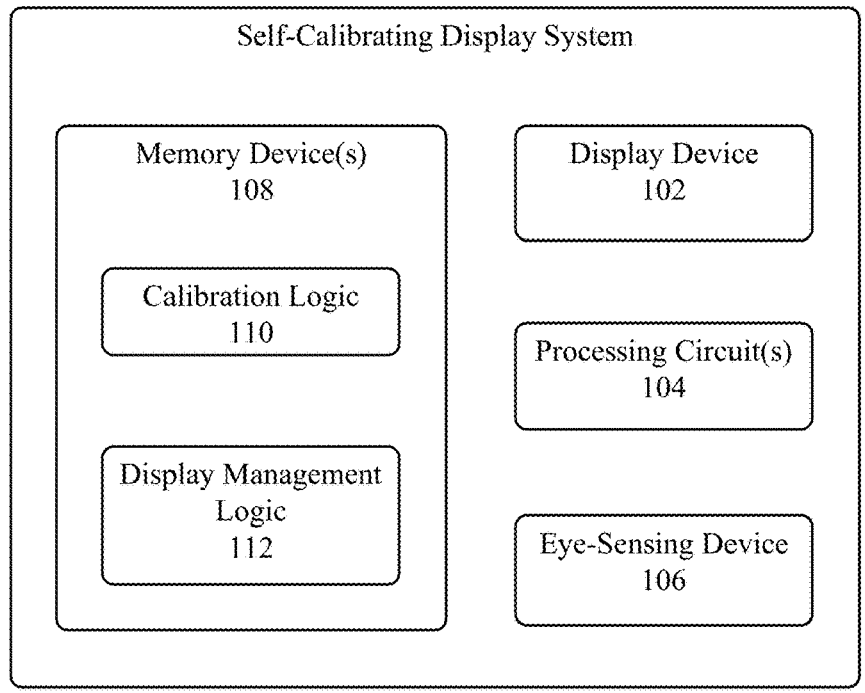
FIG. 1 is a block diagram of a self-calibrating display system, according to an example embodiment.

The features and advantages of the various embodiments will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an

DETAILED DESCRIPTION

I. Introduction

The following detailed description discloses numerous example embodiments. The scope of the present patent application is not limited to the disclosed embodiments, but also encompasses combinations of the disclosed embodiments, as well as modifications to the disclosed embodiments.

References in the specification to "one embodiment," "an embodiment," "an example embodiment," or the like, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of persons skilled in the relevant art(s) to implement such feature, structure, or characteristic in connection with other embodiments whether or not explicitly described.

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which it is intended.

Numerous exemplary embodiments are described as follows. It is noted that any section/subsection headings provided herein are not intended to be limiting. Embodiments are described throughout this document, and any type of embodiment may be included under any section/subsection. Furthermore, embodiments disclosed in any section/subsection may be combined with any other embodiments described in the same section/subsection and/or a different section/subsection in any manner.

Section II below will describe example embodiments for self-calibrating display systems. In particular, sub-section A of Section II describes an example self-calibrating display system, sub-section B of Section II describes example self-calibrating display systems that may be implemented in server-based environments, and sub-section C of Section II describes an example self-calibrating display system that includes a machine learner. Sub-section D of Section II below will describe an example mobile device and computer system in which embodiments may be implemented.

Section III below will describe some additional example embodiments. Section IV will provide some concluding remarks.

II. Example Embodiments for Self-Calibrating Display Systems

Example embodiments for self-calibrating display systems provide an improved reading or viewing experience for users based on their eyes. Each person has a unique set of eyes and power of accommodation of the eyes, a process by which certain eye muscles (e.g., ciliary muscles) contract and relax to change the focal length of the eyes such that an image of a distant or near object is clearly formed on the retina. The eye muscles are unique for everyone; thus, the power of accommodation is also different for everyone. Visual acuity, the clarity of vision, is also different for everyone depending on optical and neural factors. The extent of pupil dilation may indicate a person's interest, attention, cognitive load, mental processes, etc. Thus, in accordance with embodiments, visual acuity and pupillary information (e.g., pupil dilation or pupil size) may be determined for a person and used to automatically calibrate a display screen particularly for that person.

In accordance with further embodiments, other data may be used to enhance the accuracy of the interpretation of the pupillary information. For example, demographic data of a person (e.g., age, gender, ethnicity, location, vision correction requirement, reading comprehension level, etc.) may be used to assist in automatically calibrating a display screen for that person. Such data may be used, for example, to help to understand emotional responses to displayed content, which can impact pupil size. For instance, looking at a picture of a flag of one's own country may cause the pupil to dilate. A location or geolocation of a person may also provide useful data for automatic display calibration. For example, the size and shape of the eyes of a Chinese person may be different from that of an Indian person.

Accordingly, embodiments described herein use visual acuity and pupillary information of a user of a display device to automatically calibrate the display device, while accounting for unique eye characteristics of the user, to provide the user with an improved reading or viewing experience. For example, eye strain may be alleviated for a major part of a user's day during which he/she may be subjected to the most eye strain due to continuous computer usage at work. When eye strain is caused by mental overload, this may be detected by the constriction of the pupils, and the display device may be calibrated accordingly. For example, a font size or a screen resolution may be automatically adjusted to mitigate the eye strain. For a user who has vision issues requiring glasses, that user may be able to work at his/her computer without wearing glasses because his/her vision correction requirements may be met through the display calibration process with the appropriate display parameter values. As another example, the pupil dilation of a user may change during the course of the day because of mental work load or continuous staring at near objects. In this case, the display device may be able to accommodate the fluctuations in pupil dilation of the user by automatically adjusting the display parameter values to relieve eye strain.

By using the self-calibrating display system, the user experience is improved as eye strain and vision needs of the user may be detected and used to provide a personalized optimized reading or viewing experience. In addition, the functioning of the display device is substantially improved as it can automatically calibrate itself to accommodate the vision needs or to reduce eye strain of a user. Such automatic calibration can be highly accurate as it accounts for many different factors that may affect a user's vision. For example, factors such as visual acuity, pupillary information, and/or demographic information may be used in the calibration process to determine the appropriate display parameter value(s) for a user, which may be automatically applied to a display device. The automatic calibration process does not require the user to manually select the appropriate value for each display parameter, thereby making the process more efficient. Thus, the user can concentrate on his or her work while the display device adapts to the user's needs without the user having to manually adjust the display device. Consequently, the user can be more focused on and efficient with the tasks at hand. Furthermore, the functioning of the display device is improved because the automatic calibration process is more efficient from a computing resource perspective. In other words, fewer computing resources (e.g., processor cycles, input/output, power) may be required to automatically determine and apply the appropriate display parameter value(s) for a user.

In addition, the calibration may be provided upon a user's request or at predetermined times (e.g., periodically over time, in response to certain events (e.g., system startup), or the like). Furthermore, the process of self-calibration may include the use of a machine learner to develop a machine learning model that can take into account a wide variety of device-specific and user-specific features, wherein the machine learner may be implemented by one or more servers with training data that comes from a plethora of devices and users.

A. Example Self-Calibrating Display System

Automatic calibration of a display system may be enabled in various ways in embodiments. For instance, FIG. 1 is a block diagram of a self-calibrating display system 100, according to an example embodiment. As shown in FIG. 1, system 100 includes a display device 102 and an eye-sensing device 106, each of which may be connected to one or more processing circuits 104. Processing circuit(s) 104 may further be connected to one or more memory devices 108. System 100 is described as follows.

System 100 may be any type of system that includes at least one display for presenting visual information to a user. In accordance with certain embodiments, system 100 comprises a mobile device that has at least one display, such as but not limited to a smart phone, a Microsoft® Surface® device, a laptop computer, a notebook computer, a tablet computer such as an Apple iPad™, a netbook, or a handheld gaming device. In accordance with other embodiments, system 100 comprises a stationary device or system that has at least one display, such as but not limited to, a desktop computer, a gaming console, a television, or a smart speaker with an integrated display (e.g., an Amazon Echo Show®). In still further examples, system 100 may comprise a wearable device that has at least one display such as but not limited to a smart watch, smart glasses, a fitness tracker, a virtual reality headset, an augmented reality headset, a mixed reality headset, or the like. However, these examples are not intended to be limiting and persons skilled in the relevant art will appreciate that the techniques described herein could be broadly applied to any type of system that includes at least one display for presenting visual information to a user.

Display device 102 comprises an output device to which visual information, such as text, images and video, can be rendered so that it can be viewed by a user of system 100. Some or all of the rendering operations required to display such visual information may be performed at least in part by processing circuit(s) 104. Some or all of the rendering operations may also be performed by a display device interface such as a video or graphics chip or card (not shown in FIG. 1) that is coupled between processing circuit(s) 104 and display device 102. Depending upon the implementation of system 100, display device 102 may comprise a device that is integrated within the same physical structure or housing as processing circuit(s) 104 and memory device(s) 108 or may comprise a monitor, projector, headset, or other type of device that is physically separate from a structure or housing that includes such components and is connected thereto via a suitable wired and/or wireless connection.

Display device 102 may include a screen that is built using any of a variety of display technologies, both known or developed in the future. For example, display device 102 may include an electroluminescent display, a liquid crystal display, a light-emitting diode display, a plasma display, a quantum dot display, or the like. Display device 102 may also include an integrated input device such as a touch screen that is operable to accept user input, such as touch-based gestures.

Processing circuit(s) 104 may include one or more microprocessors, each of which may include one or more central processing units (CPUs) or microprocessor cores. Processing circuit(s) 104 may also include a microcontroller, application-specific integrated circuit (ASIC), and/or field-programmable gate array (FPGA). Processing circuit(s) 104 may operate in a well-known manner to execute computer programs (also referred to herein as computer program logic). The execution of such computer program logic may cause processing circuit(s) 104 to perform operations, including operations that will be described herein. Each component of system 100, such as display device 102, memory device(s) 108 and eye-sensing device 106 may be connected to processing circuit(s) 104 via one or more suitable interfaces.

Eye-sensing device 106 may comprise a device that utilizes any of a variety of sensors (e.g., optical sensors or cameras) to sense a human eye or a portion thereof and/or to collect and determine eye characteristics. For example, eye-sensing device 106 may comprise one or more of a pupilometer, an eye-tracker, or an eye-gazing device. For example, eye-sensing device 106 may comprise a pupilometer that monitors a pupil response, such as an amount of dilation of a pupil in response to a visual stimulus. The pupilometer may include one or more cameras that obtain an image of the eyes to determine pupillary information. The pupilometer may measure eye characteristics such as latency of constriction, constriction and dilation velocity, percentage change, and time to reach a certain threshold of constriction.

Eye-sensing device 106 may also comprise an eye tracker (e.g., Tobii Pro manufactured by Tobii Technology, Inc.) that includes multiple components, such as cameras, projectors and algorithms, for performing various tasks. For example, with an eye tracker, the projectors may create patterns of near-infrared light on the user's eye or eyes. The cameras may capture high-frame-rate images of the user's eyes as well as the patterns. The images may then be processed using processing algorithms to find specific details concerning the user's eyes and reflection patterns. Based on the gathered data, mathematical algorithms may be used to make eye calculations, such as position and gaze point on a display screen. The eye tracker may also be used to provide data about the distance between the eye and the sensor, and from this data, pupil size may be calculated by multiplying a measurement of the diameter of the pupil on the image by a scaling factor. Pupil size may be defined in various manners. For example, pupil size may be the actual, internal physical size of the pupil. Through an eye tracking session, pupil size information and its variation over time may be determined. The eye tracker can provide data that relate to basic visual behavior, such as fixation duration, saccade length, and visit counts. Based on such data, the eye tracker may produce similar measurements as those produced by a pupilometer.

Depending on the type and model of the eye-sensing device used in the calibration process, certain data or calculation methods may be used for that particular eye-sensing device to obtain the most accurate pupillary measurement. For example, certain eye-sensing devices may require a detected pupil dilation measurement to be multiplied by a scaling factor to compensate for an angle at which the image of the pupil is taken, a user emotional response, geolocation effect on eye structure or other effects.

Memory device(s) 108 include one or more volatile and/or non-volatile memory devices. Memory device(s) 108 store a number of software components (also referred to as computer programs), including calibration logic 110 and display management logic 112, that can be executed by processing circuit(s) 104. Memory device(s) 108 may also store a plurality of applications and an operating system. Each application comprises a computer program that a user of system 100 may cause to be executed by processing circuit(s) 104 to perform certain operations, wherein the type of operations to be performed may vary depending upon how the application is programmed. The operating system includes a set of computer programs that manage resources, such as display device 102, and common services for the applications that are executed by processing circuit(s) 104. Calibration logic 110, when executed by processing circuit(s) 104, causes processing circuit(s) 104 to automatically calibrate various parameters associated with display device 102. Display management logic 112, when executed by processing circuit(s) 104, causes processing circuit(s) 104 to manage display device 102, including applying the calibrated parameters to display device 102. Calibration logic 110 and/or management logic 112 may each comprise part of the aforementioned operating system or any of the aforementioned applications. Calibration logic 110 and management logic 112 will be further described in connection with subsequent figures.

Figure 2:
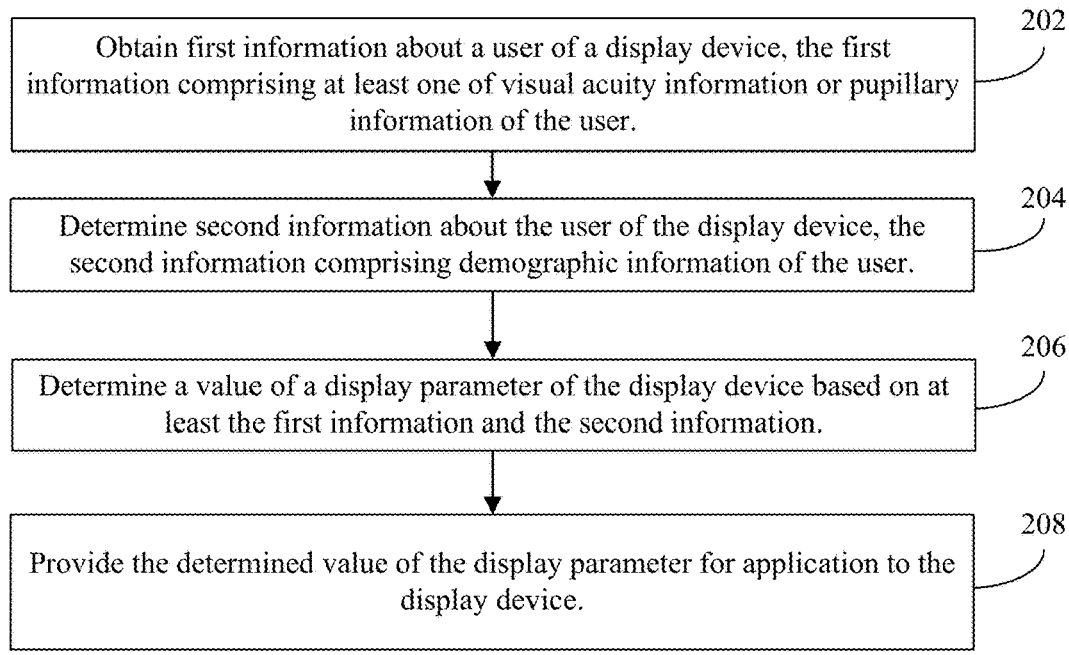
FIG. 2 depicts a flowchart of a method for calibrating a display device, according to an example embodiment.

Self-calibration of a display device may be performed in a variety of ways according to embodiments. For instance, FIG. 2 shows a flowchart 200 of a method for calibrating a display device, according to an embodiment. Flowchart 200 may be performed by calibration logic 110 of FIG. 1 when calibration logic 110 is executed by processing circuit(s) 104, for example. However, the method of flowchart 200 is not limited to the embodiment shown in FIG. 1. Further structural and operational embodiments will be apparent to persons skilled in the relevant art(s) based on the discussion regarding flowchart 200. Flowchart 200 is described as follows.

Flowchart 200 begins with step 202. In step 202, first information is obtained about a user of a display device, the first information comprising at least one of visual acuity information or pupillary information of the user. For instance, calibration logic 110 may obtain visual acuity information of a user of display device 102. Visual acuity information may be any data that relates to a clarity or sharpness of vision for the user and may be obtained at various times, such as upon a user's request, during initialization of system 100 or display device 102, during startup of an operating system or application executed by processing circuit(s) 104, or at predefined intervals.

In one embodiment, calibration logic 110 obtains visual acuity information by presenting and/or simulating a vision or visual acuity test to the user via a display device, such as display device 102. Any type of visual acuity test may be used, such as an E chart, a Jaeger chart, a Lea test, a LogMAR chart, etc. For example, a Snellen test includes a complete or partial chart of letters (or symbols/optotypes) with the letters being of different sizes and arranged in rows, each corresponding to a visual acuity fraction. The top row of the chart may include a large letter and subsequent rows may have increasing numbers of letters that decrease in size. For the Snellen test, visual acuity may be measured with a visual acuity fraction with the numerator specifying the testing distance and the denominator specifying the letter size in relation to letters on the 20/20 line, thus the 20/100 letters are 5 times larger than the 20/20 letters. As a specific example, when the Snellen chart is presented 20 feet away from the user and the user can only see the top row, the visual acuity of that user is 20/200. Thus, visual acuity information may be obtained by soliciting and receiving user input concerning the visual acuity test, for example, how well the user sees symbols of the visual acuity test or a smallest row the user can read from a particular distance.

As noted above, calibration logic 110 may alternatively or additionally obtain pupillary information of the user of display device 102 during step 202. For example, calibration logic 110 may utilize eye-sensing device 106 to obtain pupillary information of the user. Pupillary information may be obtained at various times, such as upon a user's request, during initialization of system 100 or display device 102, during startup of an operating system or application executed by processing circuit(s) 104, or at predefined intervals. Pupillary information may be obtained while certain content, including but not limited to a visual acuity test, is being presented to the user via display device 102. Pupillary information may be used independently or combined with visual acuity information by calibration logic 110. In example embodiments, visual acuity information may be obtained by presenting a visual acuity test to the user, and pupillary information may be obtained using an eye-sensing device to determine a pupil size, pupil dilation or aberration in dilation while the user is viewing the visual acuity test. Accordingly, the pupillary information obtained during the presentation of the visual acuity test along with the user feedback provided during the visual acuity test may provide more corroborative and accurate information regarding the visual acuity of the user than just the user feedback alone.

Referring back to the method of flowchart 200, in step 204, second information is determined about the user of the display device, the second information comprising demographic information of the user. For instance, calibration logic 110 may determine second information about the user of display device 102, wherein such second information comprises demographic information of the user. Demographic information of the user may be used, for example, to enhance an interpretation of pupillary information obtained during step 202. The demographic information may include, for example and without limitation, one or more of age, gender, ethnicity, location or geolocation, vision correction requirement, reading comprehension level or education level of the user. For example, ethnicity and/or geolocation may provide useful information about a user's eye, and therefore can be a factor in calculating pupil size or pupil dilation. As another example, an education level or reading comprehension level for a user may be helpful in determining whether any eye strain being detected is related to prolonged display device use or simply because the user is viewing reading material that is in a non-native language or is too complex. Vision changes with age, thus an age of the user may be helpful in calibrating a display device for that user.

Calibration logic 110 may determine demographic information of the user in a variety of ways. For example, the user may input the demographic information into system 100 or some other system that stores demographic information in a manner such that it is accessible to calibration logic 110 of system 100. For example, the user may input demographic information that is stored as part of a user profile that is then made accessible to calibration logic 110 of system 100. As another example, certain demographic information such as location or geolocation may be determined from location-based sensing devices or technology incorporated into system 100 (e.g., GPS or WiFi based location sensors), determined based on an IP address associated with system 100, or the like. Still further, demographic information concerning the user can be determined based on data captured by one or more sensors included in system 100. However, these examples are not intended to be limiting, and still other methods may be used by calibration logic 110 to obtain demographic information of the user.

In step 206, a value of a display parameter of the display device is determined based on at least the first information and the second information. For instance, calibration logic 110 may determine a value of a display parameter of display device 102 based on at least the first information and the second information. Although step 206 refers to determining the value of a single display parameter, it is to be understood that the values of multiple display parameters may be determined during step 206.

As one example of step 206, calibration logic 110 may use visual acuity information derived from user feedback and a user's age of 62 to determine that the user's near vision needs correction, and thus may change a font size of text rendered to display device 102 to a larger font size. As another example, while presenting the user with a Snellen chart, calibration logic 110 may cause eye-sensing device 106 to capture pupillary information of the user. Based on the visual acuity and/or the pupillary information and the demographic information, calibration logic 110 may determine that the user is suffering from eye strain, and thus determine a screen brightness value that is more appropriate for the user.

In example embodiments, calibration logic 110 may employ other information or data in the calibration process to improve accuracy. This additional data may be provided by the user, detected and/or sensed by system 100, or gathered from another source. Non-limiting examples of such additional information include user input, display device specific information, user environment information, display content information, application context information, or the like.

User input may include but is not limited to explicit and implicit user input such as user feedback regarding a visual acuity test or a user's emotional response when viewing certain content (e.g., a flag of his/her own country) detectable by the dilation of the pupils. Display device specific information may include but is not limited to information such as a manufacturer and/or model of display device 102, a set of capabilities of display device 102, or a set of operating characteristics of display device 102. User environment information may include but is not limited to ambient lighting conditions around the user and/or display device 102 or other environmental factors that may influence the user's eyes or vision. Display content information may include but is not limited to a type of content that is being presented to the user (e.g., an image of a flag or a visual acuity test). Application context information may include but is not limited to information about an application (e.g., game, spreadsheet, web browser) that the user is using when visual acuity or pupillary information is collected. The different items of information may be assigned different weights to obtain an optimal display parameter value or values for the user.

In step 208, the determined value of the display parameter is provided for application to the display device. For instance, calibration logic 110 may provide the determined value of the display parameter to display management logic 112 so that display management logic 112 can apply the determined value of the display parameter to display device 102. When multiple values are determined for multiple display parameters, all of the determined values may be provided to display management logic 1120 for application to display device 102.

In embodiments, display management logic 112 may apply the determined value to display device 102 and then prompt the user for feedback regarding the applied value. In further accordance with such embodiments, the user may accept the display parameter value without input or the user may provide explicit feedback to indicate that the value is adequate or should be modified to a level that is more comfortable for the user. The user may also simply accept the display parameter value, but within a certain window of time, keep or modify the display parameter value, thereby generating implicit user feedback. The user explicit feedback and/or any implicit feedback about the display parameter value may be collected by calibration logic 110 to improve the calibration process. Once the display parameter value has been applied and/or accepted by the user, it may remain in effect until the display device is recalibrated.

In embodiments, any of the first and second information obtained during the process described in flowchart 200 may be stored, for example, in a user profile that can then be made accessible to other self-calibrating display devices. For example, visual acuity or pupillary information of a user obtained by a first self-calibrating display device can then be leveraged by a second self-calibrating display device to perform the aforementioned calibration process for the same user. This may be particularly useful, for example, if the first self-calibrating display device comprises an eye-sensing device but the second self-calibrating display device does not. The aforementioned user profile may be stored on a server or other network-accessible computing device or system so that it can be accessed by multiple self-calibrating display devices and used to perform the aforementioned self-calibration process.

Figures 3, 4:
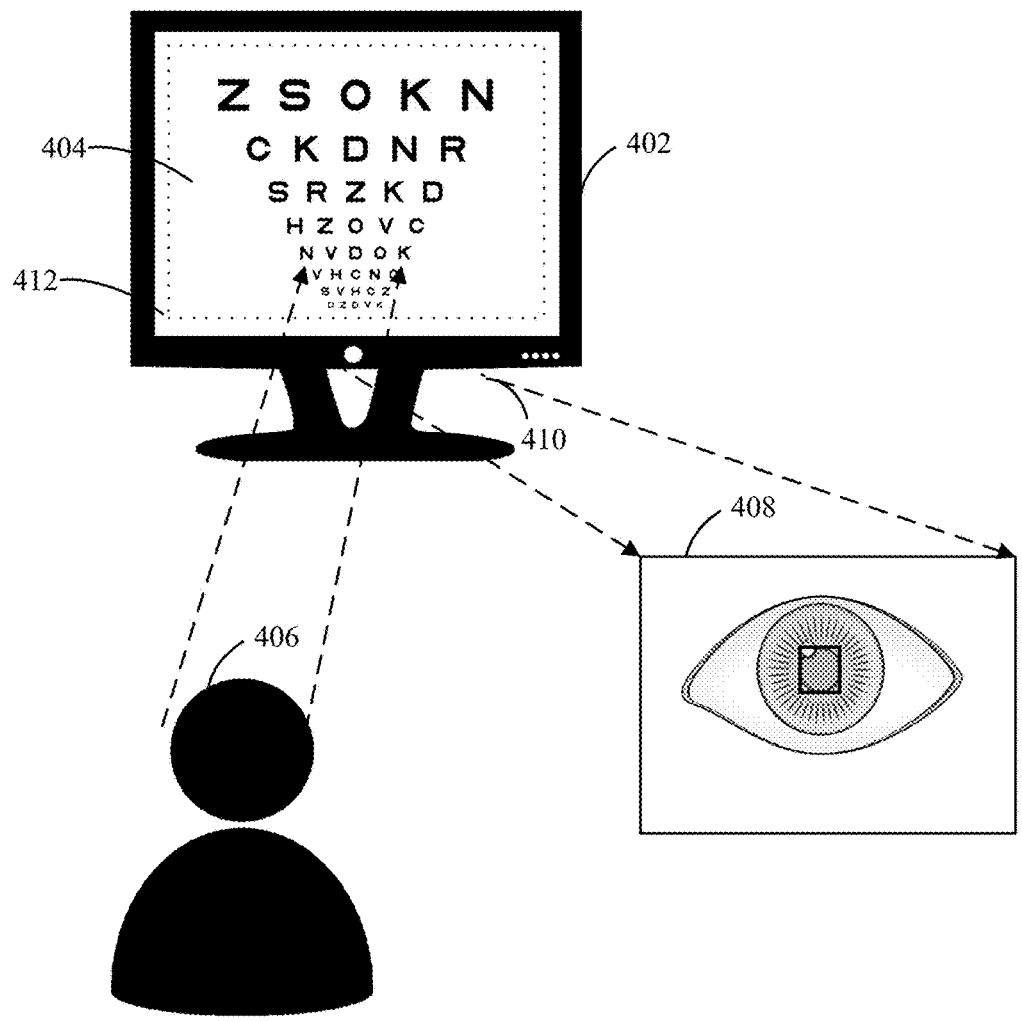
FIG. 3 depicts a list of display parameters that may be changed using the method of FIG. 2, according to an example embodiment.
FIG. 4 depicts a user environment in which a user of a display device is presented with a visual acuity test, according to an example embodiment.

Embodiments may determine many display parameters in calibrating a display device. For instance, FIG. 3 depicts a non-limiting list 300 of display parameters that may be automatically determined in accordance with an embodiment. As can be seen, non-limiting list 300 includes screen contrast, screen brightness, screen resolution, screen orientation, font size, font effect (three-dimensional appearance, spherical appearance), font orientation, color temperature, or whether certain a certain color profile or filter should be applied (including, for example, application of a color profile or filter to assist the colorblind in viewing content). Other relevant parameters that are not shown in FIG. 3 may include, for example, whether an application is displayed in a full screen, borderless full screen, or windowed mode, whether content is displayed on only one display or across multiple displays, or whether content is presented in a two-dimensional (2D) or three-dimensional (3D) form, as well as various 3D settings when content is presented in 3D form (e.g., parameters relating to ambient occlusion, anisotropic filtering, antialiasing, texture filtering or vertical sync). Where the display device comprises a virtual reality headset, an augmented reality headset, or a mixed reality headset, the display parameters may include parameters specific to those types of experiences.

Visual acuity information and pupillary information may be obtained in various way for a calibration process in a self-calibrating display system as discussed above in reference to FIGS. 1 and 2. As a specific example, FIG. 4 depicts a user environment 400 in which a user of a display device may be presented with a visual acuity test, according to an example embodiment. User environment 400 includes a self-calibrating display system 402, which may be one implementation of self-calibrating display system 100 of FIG. 1. System 402 may include a display screen 412 configured to present content to a user 406. In FIG. 4, display screen 412 is presenting a visual acuity test 404, in the form of a Snellen chart, to user 406. User 406 may be instructed to step away from display screen 412 to a required distance in order to improve the accuracy of the results for visual acuity test 404. When user 406 has stepped away from display screen 412, user 406 may provide input to system 402 via any suitable means available, such as via a mouse, a keyboard, an audio and/or video input device, each of which may be integrated with system 402 or separate from but communicatively connected to system 402. For example, wireless our audio input device may be leveraged to provide input to system 402 from a distance when the user cannot easily access a keyboard or mouse of the system. As user 406 views visual acuity test 404, an eye-sensing device 410 may sense eye characteristics of the user, for example, by capturing an image 408 of at least one eye of user 406. In embodiments, multiple images of the eye(s) of user 406 may be captured. Data from image 408 may be used by display system 402 to obtain pupillary information for user 406. Display system 402 may also obtain feedback from user 406 regarding how well user 406 sees visual acuity test 404 to determine visual acuity information for user 406. Pupillary information and visual acuity information, alone or in combination, may be used by display system 402 to determine one or more display parameter values that would provide an improved or optimal reading/viewing experience for user 406. In embodiments and as described above, additional data may be used in the calibration process by display system 402 to perform this function.

Figure 5:
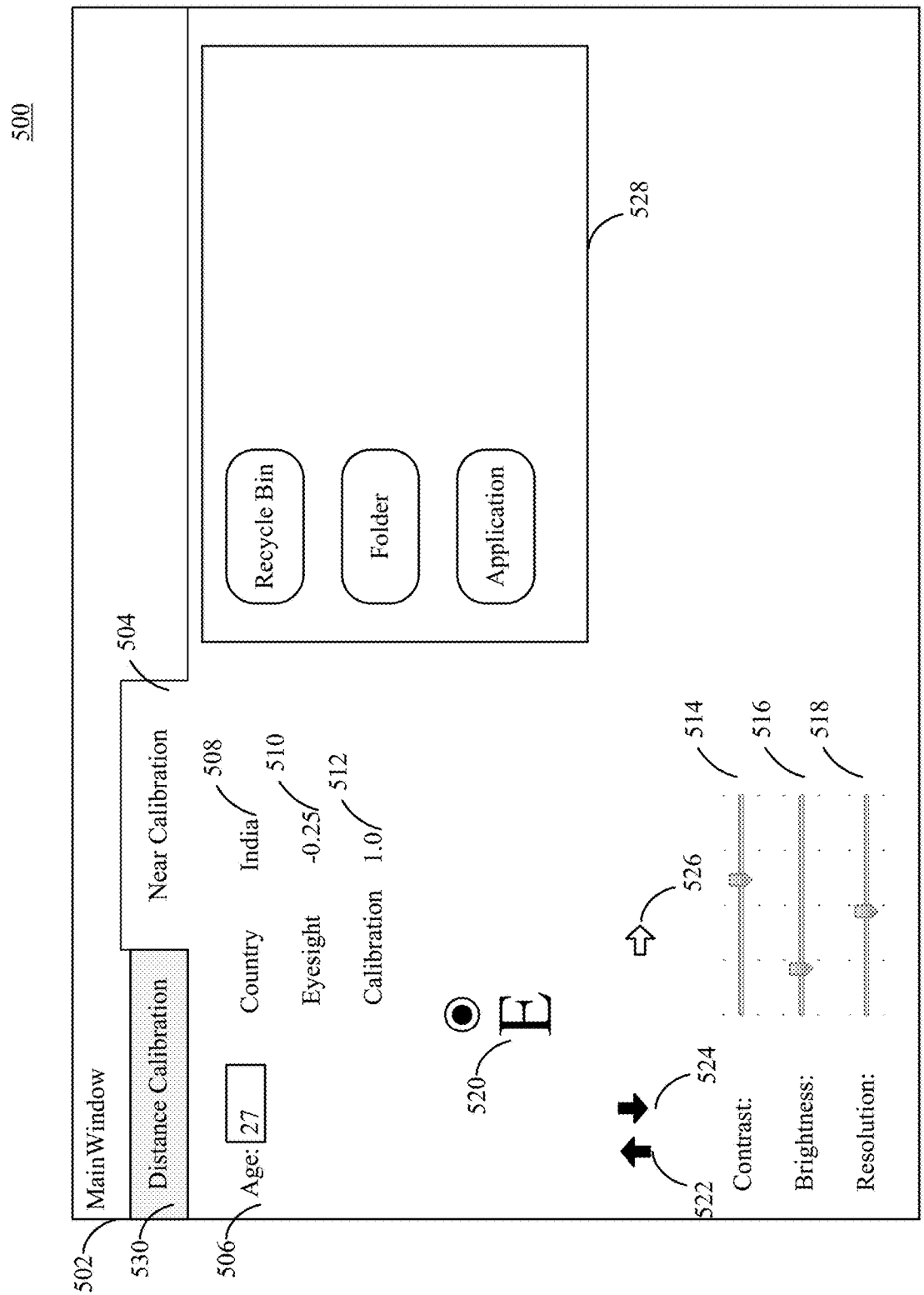
FIG. 5 depicts a user interface that facilitates a display device configuration process according to an example embodiment.

Additional approaches may be used to implement the calibration process. For example, FIG. 5 depicts a user interface 500 that can be used to facilitate a display device calibration process according to an example embodiment. User interface 500 may comprise, for example, a user interface for an application or an operating system. User interface 500 may be displayed to a user on a display screen of a self-calibration display system, such as system 100 of FIG. 1. User interface 500 may be displayed during the calibration process to present a visual acuity test, to obtain user input, and/or to provide instructions to the user.

User interface 500 may include a main window 502 that has two tabs, a distance calibration tab 536 and a near calibration tab 504, which is shown as an active tab. Near calibration tab 504 includes information that relates to the near vision or calibration of a user of a display system. For example, near calibration tab 504 includes fields that may be prepopulated by the display system, for example using information from previous calibrations or information from a user profile. Additionally, the user of the display system may enter information into the fields to provide new information or to correct stale information, thereby providing the most accurate information for use in the calibration process. For example, these fields may include an age field 506 for an age of the user, a country field 508 for a country of origin of the user, an eyesight field 510 for vision value(s) related to a prescription for a pair of glasses or contact lens (e.g., Diopter, spherical, cylinder, axis, base curve, diameter, etc.), a calibration field 512 for identifying information for a calibration. In addition, a visual acuity test 520 may be presented to the user during the calibration process. Up arrow 522, down arrow 524 and right arrow 526 may be used by the user to navigate through visual acuity test 520 and/or to provide user feedback regarding how well the user can see the symbols of the visual acuity test 520. In addition, sliders may be presented to inform the user of the selected display parameter settings as well as to enable the user to change the settings. The sliders may include a contrast slider 514, a brightness slider 516, and a resolution sider 518. The information depicted on near calibration tab 504 is not intended to be limiting as more or less information may be presented. Also, the information may be presented using forms other than what is depicted, for example, buttons may be used instead of sliders.

Main window 502 may also include a window 528 to enable the user to view other content during the calibration process, such as a desktop of the user, an image of a flag or other visual stimuli. Distance calibration tab 530 may present information similar to what is depicted for tab 504 but related to the distance vision or calibration for the user.

B. Examples of Server-Based Self-Calibrating Display Systems

Figure 6:
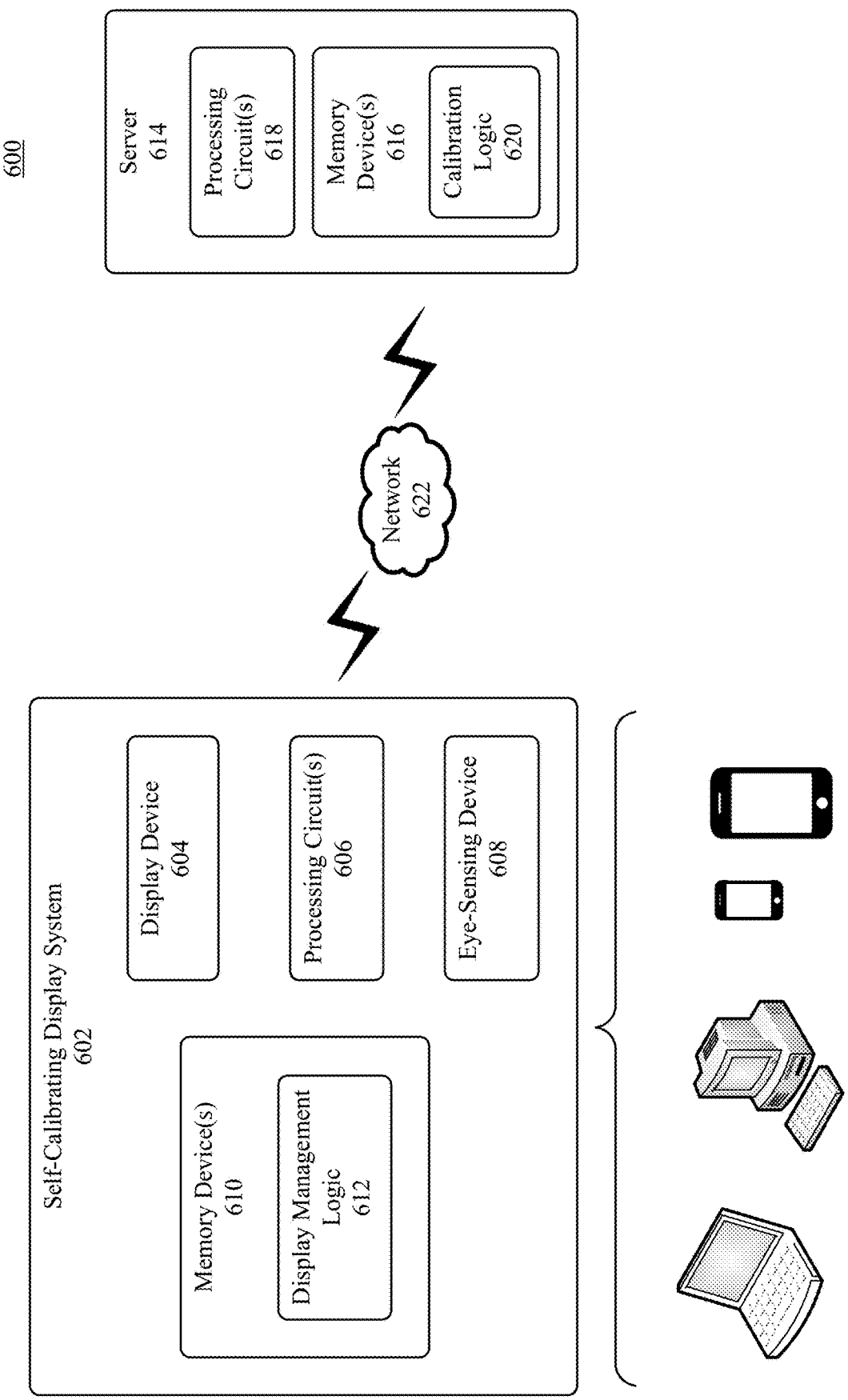
FIG. 6 is a block diagram of a system for automatically calibrating a display device, according to an example embodiment.

Automatic calibration of a display system may be implemented using an architecture that is different from that used by system 100 depicted in FIG. 1. For example, FIG. 6 is a block diagram of a system 600 for automatically calibrating a display device, according to an example embodiment. System 600 may include a self-calibrating display system 602 and a server 614 to which system 602 is communicatively connected via a network 622. Server 614 may comprise, for example, an enterprise server, a public or private cloud server, or some other type of server.

System 602 and server 614 may each include one or more wired or wireless network interfaces to enable communication with each other and with other devices over network 622. Examples of such interfaces include a Bluetooth™ interface, a near field communication (NFC) interface, an IEEE 802.11 wireless LAN (WLAN) wireless interface, a Worldwide Interoperability for Microwave Access (Wi-MAX) interface, an Ethernet interface, a cellular network interface, etc. Network 622 may include a local a local area network (LAN), a wide area network (WAN) such as the Internet, a personal area network (PAN), and/or a combination of communication networks.

Like system 100 described above in reference to FIG. 1, system 602 may be any type of system that includes at least one display for presenting visual information to a user. Thus, as shown in FIG. 6, system 602 may comprise a laptop or notebook (Microsoft® Surface®) computer, a desktop computer, a smart phone, a tablet or any device that includes eye-sensing capability. However, these examples are not intended to be limiting.

System 602 includes a display device 604, processing circuit(s) 606, an eye-sensing device 608, and memory device(s) 610 that includes display management logic 612. These components are similar to the components of system 100 of FIG. 1, thus they will not be described again for the sake of brevity. The main difference between system 602 and system 100 is that certain components of system 602 may reside in one or more separate devices and/or systems. For example, calibration logic 620 may reside in memory device(s) 616 of server 614 where it may be executed by processing circuit(s) 618 of server 614.

Thus, in accordance with this implementation, the functionality of calibration logic 620 may be provided as an on-demand service by server 614 to system 602 as well as to other self-calibrating display systems (not shown in FIG. 6). For example, system 602 may invoke calibration logic 620 of server 614 by placing a suitable API call thereto via network 622 and may pass various information to calibration logic 620 as part of that or one or more separate API calls. The information that may be passed may include any of the information described above in reference to FIG. 2 (e.g., visual acuity information, pupillary information, demographic information, etc.) that may be used in making a display parameter determination. After making a display parameter determination, calibration logic 620 may send an API response back to system 602 via network 622 that includes the determined values of one or more display parameters. Such display parameter values may then be applied to display device 604 by display management logic 612 executing on system 602.

Figure 7:
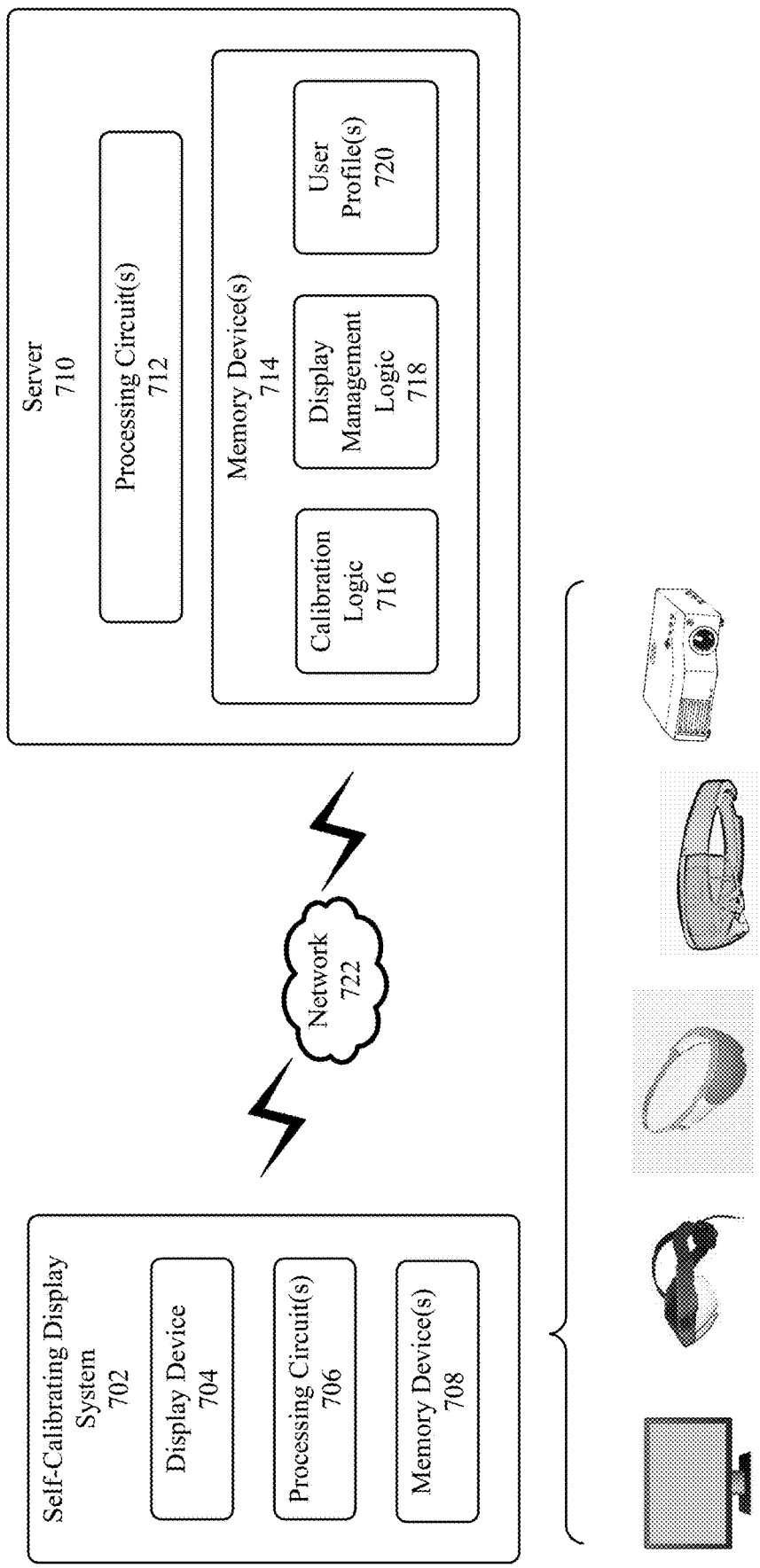
FIG. 7 is block diagram of another system for automatically calibrating a display device, according to an example embodiment.

Automatic calibration of a display system may further be implemented using another architecture that is different from that used by system 100 depicted in FIG. 1. For example, FIG. 7 is a block diagram of a system 700 for automatically calibrating a display device, according to an example embodiment. System 700 may include a self-calibrating display system 702 and a server 710 to which system 702 is communicatively connected via a network 722. Server 710 may comprise, for example, an enterprise server, a public or private cloud server, or some other type of server. System 702 and server 710 may each include one or more wired or wireless network interfaces to enable communication with each other and with other devices over network 722. Examples of such interfaces include a Bluetooth™ interface, a near field communication (NFC) interface, an IEEE 802.11 wireless LAN (WLAN) wireless interface, a Worldwide Interoperability for Microwave Access (Wi-MAX) interface, an Ethernet interface, a cellular network interface, etc. Network 722 may include a local a local area network (LAN), a wide area network (WAN) such as the Internet, a personal area network (PAN), and/or a combination of communication networks.

Like system 100 described above in reference to FIG. 1, system 702 may be any type of system that includes at least one display for presenting visual information to a user, although system 702 may be more streamlined with fewer components than system 100. In embodiments, system 702 may be dependent on some other device, for example, server 710 to manage its display device 704 and may not include eye-sensing capability. Thus, as shown in FIG. 7, system 702 may comprise a laptop or notebook computer, a desktop computer, a smart phone, a tablet, a monitor, a headset (virtual reality, augmented reality, or mixed reality), or a projector. However, these examples are not intended to be limiting, and system 702 may also comprise a Microsoft® Surface® device, a netbook, a handheld gaming device, a gaming console, a television, a smart speaker with an integrated display (e.g., an Amazon Echo Show®), a smart watch, smart glasses, a fitness tracker or any other system that includes at least one display for presenting visual information to a user.

System 702 may include a display device 704, and may optionally include processing circuit(s) 706 and memory device(s) 708. Display device 704 may include a display screen to which visual information, such as text, images and video, can be rendered so that it can be viewed by a user of system 702. Processing circuit(s) 706 may include one or more microprocessors or microcontrollers. Processing circuit(s) 706 may operate in a well-known manner to execute computer programs. Memory device(s) 708 may include one or more volatile and/or non-volatile memory devices for storing software components or computer programs, such as applications and operating systems. Each computer program may be executed by processing circuit(s) 706 to perform operations. The operating system includes a set of computer programs that manage resources, such as display device 704.

Server 710 may comprise any number of computing devices and may include any type of computing and networking resources. Server 710 may be configured to provide one or more services (including microservices), applications, and/or supporting services. Server 710 may include memory device(s) 714, which may store calibration logic 716, display management logic 718 and user profile(s) 720. Calibration logic 716 and display management logic 718 stored in memory device(s) 714 may be executed by processing circuit(s) 712 to perform programmed operations.

In embodiments, any information that is determined and/or obtained during the calibration process (e.g., flowchart 200 shown in FIG. 2) may be stored in user profile(s) 720, each of which may correspond to a user of a display device with eye-sensing capability and/or the ability to perform a visual acuity test. User profile(s) 720 may be stored in sever 710 and made accessible to other self-calibrating devices, including those that do not have eye-sensing capability and/or the ability to perform a visual acuity test, such as system 702. For example, visual acuity, pupillary information, or demographic information of a user obtained by a desktop computer with an eye tracker may be leveraged by a virtual-reality headset that may not have eye-sensing capability to determine an appropriate set of display parameters to be used by the virtual-reality headset for that user in accordance with this embodiment.

The functionality of calibration logic 716 and display management logic 718 may be provided as one or more on-demand services by server 710 to system 702 as well as to other self-calibrating display systems (not shown in FIG. 7). For example, system 702 may invoke calibration logic 716 of server 710 by placing a suitable API call thereto via network 722 and may pass various information to calibration logic 716 as part of that or one or more separate API calls. The information that may be passed may include any information that may be used in making a display parameter determination, for example, user input, display device information, user environment information, display content information or application context information. After making a display parameter determination, calibration logic 716 may pass the display parameter determination to display management logic 718 that is also executing on server 710. Display management logic 718 may then manage display device 704, for example, by sending and/or applying the display parameter determination and/or display parameter values to display device 704, for example, via one or more API calls.

C. Example of a Self-Calibrating Display System Having a Machine Learner

Automatic calibration of a display system may also be enabled with the aid of an artificial intelligence algorithm that is trained or otherwise configured in a cloud or server-based environment. For example, FIG. 8 is a block diagram of a self-calibrating display system 800 that includes a machine learner, according to an example embodiment.

System 800 includes a server 802 and one or more client devices, such as a smart television 810, a laptop 812, a desktop personal computer 814, a tablet 816, a smart phone 818, a projector 820, a mixed reality headset 822, an augmented reality headset 824, or a virtual reality headset 826. The client devices and server 802 may each include one or more wired or wireless interfaces to enable communication with each other and with other devices either in a peer-to-peer manner or over network 808. Examples of such interfaces include a Bluetooth™ interface, a near field communication (NFC) interface, an IEEE 802.11 wireless LAN (WLAN) wireless interface, a Worldwide Interoperability for Microwave Access (Wi-MAX) interface, an Ethernet interface, a cellular network interface, etc. Network 808 may include a local a local area network (LAN), a wide area network (WAN) such as the Internet, a personal area network (PAN), and/or a combination of communication networks. Each of the client devices may include an architecture similar to system 100 shown in FIG. 1 or display systems 602 or 702 respectively shown in FIGS. 6 and 7, and thus may operate in a similar manner.

Server 802 may include one or more processing circuits and one or more memory devices. The memory device(s) of server 802 may store computer programs including a machine learner 804 and may also store a model 806. Machine learner 804 may comprise computer program logic that, when executed by the processing circuit(s), causes the processing circuit(s) to accept training data input and use such training data input to obtain or update model 806. Model 806 may comprise an algorithm that determines display parameter values for calibrating a display device as a function of various features. A programmer may initially provide a first iteration of model 806. Training data may be provided to machine learner 804 and may include the values of display parameters for different devices, along with various features associated with those values. For example, training data may indicate that a particular set of display parameter values is associated with particular set of values for the following features: visual acuity information for a user, pupillary information for the user, user input (e.g., user feedback regarding a visual acuity test or an applied display parameter), demographic information for the user (e.g., age, gender, ethnicity, location or geolocation, vision correction requirement, reading comprehension level, etc.), display device specific information (display device manufacturer and/or model, display device capabilities or operating characteristics), user environment information (e.g., ambient lighting information), display content information (e.g., an indication or classification of content being displayed to the user), and/or application context information. Such example features are shown in list 900 of FIG. 9.

Figure 8:
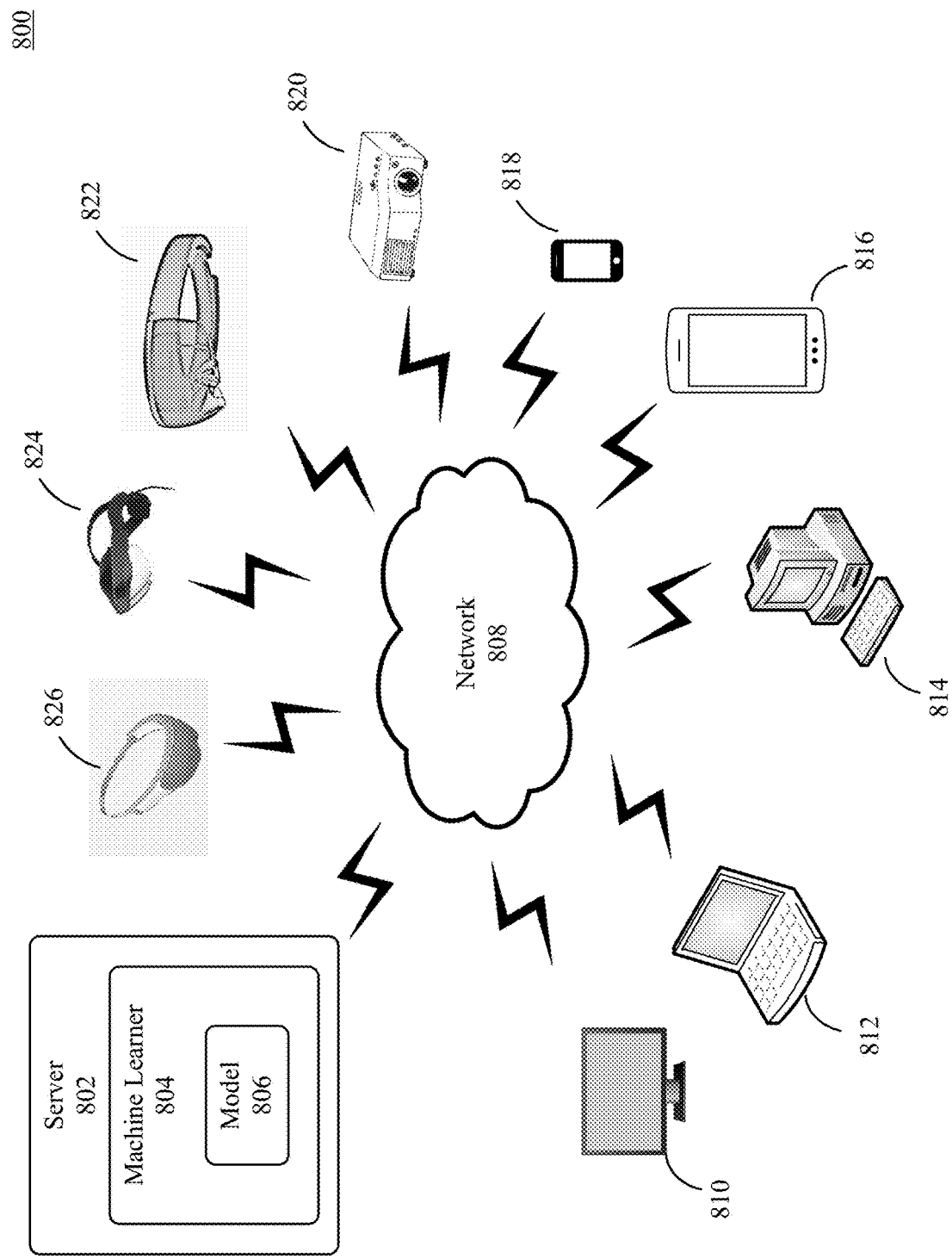
FIG. 8 is a block diagram of a self-calibrating display system that includes a machine learner, according to an example embodiment.

Training data may be collected from multiple sources, such as from the client devices shown in FIG. 8. As more training data is incorporated by machine learner 804, machine learner 804 may train model 806 such that model 806 becomes more sophisticated and accurate in its prediction of display parameter values over time. For example, if machine learner 804 learns that gender is not a highly relevant factor in determining display parameter values, machine learner 804 may lower a weight associated with the gender feature in model 806. Once a high degree of confidence of model 806 is reached, model 806 may be deployed for wider use. For example, model 806 may be deployed to system 100 of FIG. 1 and used by calibration logic 110 to select display parameter values as a function of various features. Likewise, model 806 may be deployed to server 614 of FIG. 6 and used by calibration logic 620 to select display parameter values as a function of various features. Similarly, model 806 may be deployed to server 710 of FIG. 7 and used by calibration logic 716 to determine display parameter values as a function of various features. However, as more training data is collected, machine learner 804 may continue to update model 806 as needed. Updated models can then be further deployed to various self-calibrating display systems.

A self-calibrating display system may use model 806 in various ways. For example, FIG. 10 depicts a flowchart 1000 of a method for calibrating a display using a model obtained through machine learning, according to an example embodiment. Flowchart 1000 may be performed by calibration logic 110 of system 100, for example. However, the method of flowchart 1000 is not limited to this embodiment. Further structural and operational embodiments will be apparent to persons skilled in the relevant art(s) based on the discussion regarding flowchart 1000. Flowchart 1000 is described as follows.

Flowchart 1000 begins with step 1002. In step 1002, a plurality of features is obtained, wherein one of the plurality of features comprises visual acuity information or pupillary information for a user of a display device. For example, calibration logic 110 may obtain features that include visual acuity information and pupillary information for the user as described above in connection with FIGS. 1-5, as well as other features that include or are derived from user input, demographic information for the user, display device specific information, user environment information, display content information, and/or application context information.

In step 1004, the plurality of features is provided as inputs to a model obtained through machine learning that determines a value of a display parameter of the display device based on the plurality of features. For example, calibration logic 110 may provide the visual acuity information, pupillary information and additional data as inputs to a model 806 that is obtained through machine learning by machine learner 804. Model 806 may then determine a value of a display parameter based on the plurality of features. For instance, model 806 may take as inputs a visual acuity information of a tablet user as having 20/20 vision, an age of the user as being 27 and determine that a font size of 12 would be the optimal font size for the user.

In step 1006, the determined value of the display parameter is provided for application to the display device. For example, calibration logic 110 may provide the value of the display parameter as determined by model 806 to display management logic 112, and display management logic 112 may apply the display parameter to display device 102. To continue with the above example, the font size value of "12" may be provided by calibration logic 110 to display management logic 112 for application to display device 102.

In many cases, additional information such as user feedback is of great value in continually updating a machine learned model. For instance, FIG. 11 shows a flowchart 1100 of a method for providing information as training data to a machine learner, according to an example embodiment. Flowchart 1100 may be performed by system 800 shown in FIG. 8, for example. However, the method of flowchart 1100 is not limited to that embodiment. Further structural and operational embodiments will be apparent to persons skilled in the relevant art(s) based on the discussion regarding flowchart 1100.

In step 1102 of flowchart 1100, an indication of a user's acceptance or rejection of a determined value of a display parameter is provided as training data to a machine learner to update the model. For instance, feedback data in the form of an indication of a user's acceptance or rejection of a determined value of a display parameter may be provided from the user's display device to server 802. The feedback data may be explicitly provided by the user via statements, such as "Yes, I like the applied display parameter setting" or "No, I want to increase the screen brightness." The feedback data may also be implicitly provided, such as the user modifying the determined value for the display parameter immediately after application of that value to the display device or sometime thereafter. The feedback data then be used by machine learner 804 to update model 806 to enable more accurate calibration of display devices over time.

In example embodiments, user feedback data regarding the applied display parameter may be collected from many users and/or devices, such as the client devices shown in FIG. 8 as training data for machine learner 804.

D. Example Mobile Device and Computer System Implementation

Embodiments described herein may be implemented in hardware, or hardware combined with software and/or firmware. For example, embodiments described herein may be implemented as computer program code/instructions configured to be executed in one or more processors and stored in a computer readable storage medium. Alternatively, embodiments described herein may be implemented as hardware logic/electrical circuitry.

As noted herein, the embodiments described, including system 100 of FIG. 1, system 600 of FIG. 6, system 700 of FIG. 7, system 800 of FIG. 8 along with any components and/or subcomponents thereof, as well as the flowcharts/flow diagrams described herein, including portions thereof, and/or further examples described herein, may be implemented in hardware, or hardware with any combination of software and/or firmware, including being implemented as computer program code configured to be executed in one or more processors and stored in a computer readable storage medium, or being implemented as hardware logic/electrical circuitry, such as being implemented together in a system-on-chip (SoC), a field programmable gate array (FPGA), or an application specific integrated circuit (ASIC). A SoC may include an integrated circuit chip that includes one or more of a processor (e.g., a microcontroller, microprocessor, digital signal processor (DSP), etc.), memory, one or more communication interfaces, and/or further circuits and/or embedded firmware to perform its functions.

Embodiments described herein may be implemented in one or more computing devices similar to a mobile system and/or a computing device in stationary or mobile computer embodiments, including one or more features of mobile systems and/or computing devices described herein, as well as alternative features. The descriptions of mobile systems and computing devices provided herein are provided for purposes of illustration, and are not intended to be limiting. Embodiments may be implemented in further types of computer systems, as would be known to persons skilled in the relevant art(s).

Figure 12:
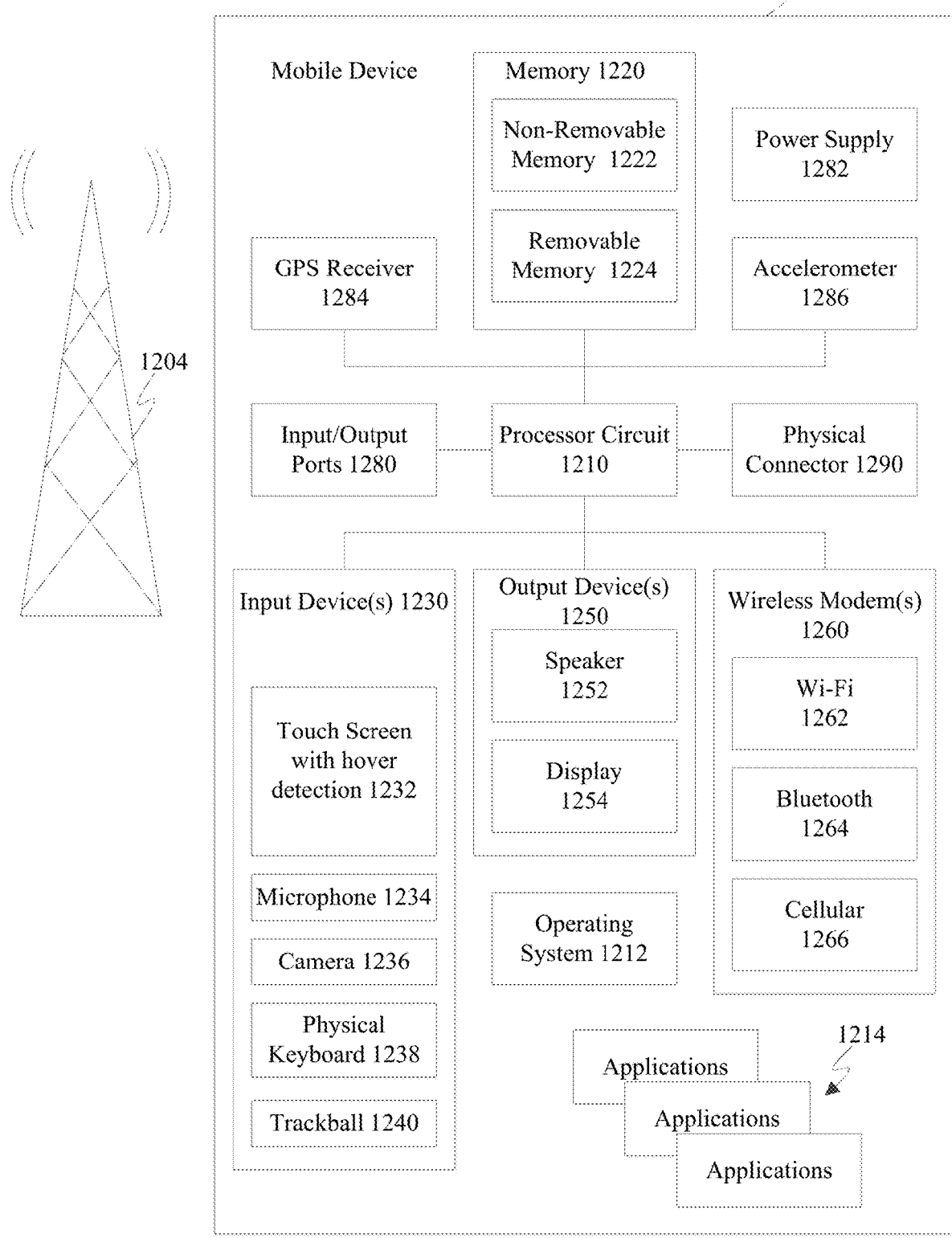
FIG. 12 is a bock diagram of an exemplary mobile device in which embodiments may be implemented.

FIG. 12 is a block diagram of an exemplary mobile system 1200 that includes a mobile device 1202 that may implement embodiments described herein. For example, mobile device 1202 may be used to implement any system, client, or device, or components/subcomponents thereof, in the preceding sections. As shown in FIG. 12, mobile device 1202 includes a variety of optional hardware and software components. Any component in mobile device 1202 can communicate with any other component, although not all connections are shown for ease of illustration. Mobile device 1202 can be any of a variety of computing devices (e.g., cell phone, smart phone, handheld computer, Personal Digital Assistant (PDA), etc.) and can allow wireless two-way communications with one or more mobile communications networks 1204, such as a cellular or satellite network, or with a local area or wide area network.

Mobile device 1202 can include a controller or processor 1210 (e.g., signal processor, microprocessor, ASIC, or other control and processing logic circuitry) for performing such tasks as signal coding, data processing, input/output processing, power control, and/or other functions. An operating system 1212 can control the allocation and usage of the components of mobile device 1202 and provide support for one or more application programs 1214 (also referred to as "applications" or "apps"). Application programs 1214 may include common mobile computing applications (e.g., e-mail applications, calendars, contact managers, web browsers, messaging applications) and any other computing applications (e.g., word processing applications, mapping applications, media player applications).

Mobile device 1202 can include memory 1220. Memory 1220 can include non-removable memory 1222 and/or removable memory 1224. Non-removable memory 1222 can include RAM, ROM, flash memory, a hard disk, or other well-known memory devices or technologies. Removable memory 1224 can include flash memory or a Subscriber Identity Module (SIM) card, which is well known in GSM communication systems, or other well-known memory devices or technologies, such as "smart cards." Memory 1220 can be used for storing data and/or code for running operating system 1212 and application programs 1214. Example data can include web pages, text, images, sound files, video data, or other data to be sent to and/or received from one or more network servers or other devices via one or more wired or wireless networks. Memory 1220 can be used to store a subscriber identifier, such as an International Mobile Subscriber Identity (IMSI), and an equipment identifier, such as an International Mobile Equipment Identifier (IMEI). Such identifiers can be transmitted to a network server to identify users and equipment.

A number of programs may be stored in memory 1220. These programs include operating system 1212, one or more application programs 1214, and other program modules and program data. Examples of such application programs or program modules may include, for example, computer program logic (e.g., computer program code or instructions) for implementing one or more of including system 100 of FIG. 1, system 600 of FIG. 6, system 700 of FIG. 7, system 800 of FIG. 8 along with any components and/or subcomponents thereof, as well as the flowcharts/flow diagrams described herein, including portions thereof, and/or further examples described herein.

Mobile device 1202 can support one or more input devices 1230, such as a touch screen 1232, a microphone 1234, a camera 1236, a physical keyboard 1238 and/or a trackball 1240 and one or more output devices 1250, such as a speaker 1252 and a display 1254. Other possible output devices (not shown) can include piezoelectric or other haptic output devices. Some devices can serve more than one input/output function. For example, touch screen 1232 and display 1254 can be combined in a single input/output device. Input devices 1230 can include a Natural User Interface (NUI).

One or more wireless modems 1260 can be coupled to antenna(s) (not shown) and can support two-way communications between processor 1210 and external devices, as is well understood in the art. Modem 1260 is shown generically and can include a cellular modem 1266 for communicating with the mobile communication network 1204 and/or other radio-based modems (e.g., Bluetooth 1264 and/or Wi-Fi 1262). At least one wireless modem 1260 is typically configured for communication with one or more cellular networks, such as a GSM network for data and voice communications within a single cellular network, between cellular networks, or between the mobile device and a public switched telephone network (PSTN).

Mobile device 1202 can further include at least one input/output port 1280, a power supply 1282, a satellite navigation system receiver 1284, such as a Global Positioning System (GPS) receiver, an accelerometer 1286, and/or a physical connector 1290, which can be a USB port, IEEE 1394 (FireWire) port, and/or RS-232 port. The illustrated components of mobile device 1202 are not required or all-inclusive, as any components can be deleted and other components can be added as would be recognized by one skilled in the art.

In an embodiment, mobile device 1202 is configured to implement any of the above-described features of flowcharts herein. Computer program logic for performing any of the operations, steps, and/or functions described herein may be stored in memory 1220 and executed by processor 1210.

Figure 13:
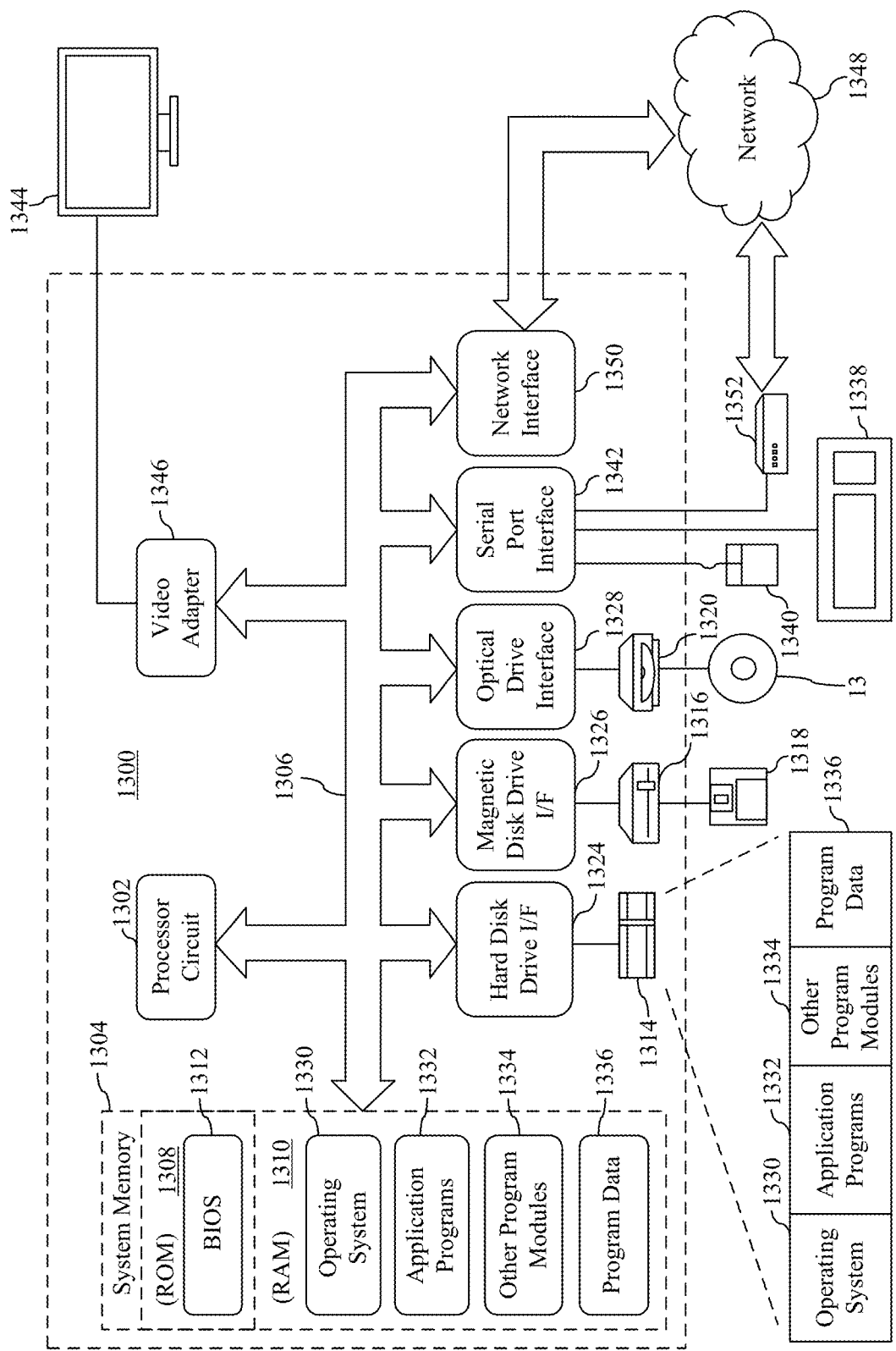
FIG. 13 is a block diagram of an example processor-based computer system that may be used to implement various embodiments.

FIG. 13 depicts an example processor-based computer system 1300 that may be used to implement various embodiments described herein. For example, system 1300 may be used to implement system 100 of FIG. 1, system 600 of FIG. 6, system 700 of FIG. 7 or system 800 of FIG. 8. System 1300 may also be used to implement any of the steps of any of the flowcharts of FIGS. 2, 10 and 11 as described above. The description of system 1300 provided herein is provided for purposes of illustration, and is not intended to be limiting. Embodiments may be implemented in further types of computer systems, as would be known to persons skilled in the relevant art(s).

As shown in FIG. 13, system 1300 includes a processing unit 1302, a system memory 1304, and a bus 1306 that couples various system components including system memory 1304 to processing unit 1302. Processing unit 1302 may comprise one or more circuits, microprocessors or microprocessor cores. Bus 1306 represents one or more of any of several types of bus structures, including a memory bus or memory controller, a peripheral bus, an accelerated graphics port, and a processor or local bus using any of a variety of bus architectures. System memory 1304 includes read only memory (ROM) 1308 and random access memory (RAM) 1312. A basic input/output system 1312 (BIOS) is stored in ROM 1308.

System 1300 also has one or more of the following drives: a hard disk drive 1314 for reading from and writing to a hard disk, a magnetic disk drive 1316 for reading from or writing to a removable magnetic disk 1318, and an optical disk drive 1320 for reading from or writing to a removable optical disk 1322 such as a CD ROM, DVD ROM, BLU-RAY™ disk or other optical media. Hard disk drive 1314, magnetic disk drive 1316, and optical disk drive 1320 are connected to bus 1306 by a hard disk drive interface 1324, a magnetic disk drive interface 1326, and an optical drive interface 1328, respectively. The drives and their associated computer-readable media provide nonvolatile storage of computer-readable instructions, data structures, program modules and other data for the computer. Although a hard disk, a removable magnetic disk and a removable optical disk are described, other types of computer-readable memory devices and storage structures can be used to store data, such as flash memory cards, digital video disks, random access memories (RAMs), read only memories (ROM), and the like.

A number of program modules may be stored on the hard disk, magnetic disk, optical disk, ROM, or RAM. These program modules include an operating system 1330, one or more application programs 1332, other program modules 1334, and program data 1336. In accordance with various embodiments, the program modules may include computer program logic that is executable by processing unit 1302 to perform any or all of the functions and features of system 100 of FIG. 1, system 600 of FIG. 6, system 700 of FIG. 7 or system 800 of FIG. 8. The program modules may also include computer program logic that, when executed by processing unit 1302, causes processing unit 1302 to perform any of the steps of any of the flowcharts of FIGS. 2, 10 and 11 as described above.

A user may enter commands and information into system 1300 through input devices such as a keyboard 1338 and a pointing device 1340 (e.g., a mouse). Other input devices (not shown) may include a microphone, joystick, game controller, scanner, or the like. In one embodiment, a touch screen is provided in conjunction with a display 1344 to allow a user to provide user input via the application of a touch (as by a finger or stylus for example) to one or more points on the touch screen. These and other input devices are often connected to processing unit 1302 through a serial port interface 1342 that is coupled to bus 1306, but may be connected by other interfaces, such as a parallel port, game port, or a universal serial bus (USB). Such interfaces may be wired or wireless interfaces.

Display 1344 is connected to bus 1306 via an interface, such as a video adapter 1346. In addition to display 1344, system 1300 may include other peripheral output devices (not shown) such as speakers and printers.

System 1300 is connected to a network 1348 (e.g., a local area network or wide area network such as the Internet) through a network interface 1350, a modem 1352, or other suitable means for establishing communications over the network. Modem 1352, which may be internal or external, is connected to bus 1306 via serial port interface 1342.

As used herein, the terms "computer program medium," "computer-readable medium," and "computer-readable storage medium" are used to generally refer to memory devices or storage structures such as the hard disk associated with hard disk drive 1314, removable magnetic disk 1318, removable optical disk 1322, as well as other memory devices or storage structures such as flash memory cards, digital video disks, random access memories (RAMs), read only memories (ROM), and the like. Such computer-readable storage media are distinguished from and non-overlapping with communication media (do not include communication media). Communication media typically embodies computer-readable instructions, data structures, program modules or other data in a modulated data signal such as a carrier wave. The term "modulated data signal" means a signal that has one or more of its characteristics set or changed in such a manner as to encode information in the signal. By way of example, and not limitation, communication media includes wireless media such as acoustic, RF, infrared and other wireless media. Embodiments are also directed to such communication media.

As noted above, computer programs and modules (including application programs 1332 and other program modules 1334) may be stored on the hard disk, magnetic disk, optical disk, ROM, or RAM. Such computer programs may also be received via network interface 1350, serial port interface 1342, or any other interface type. Such computer programs, when executed or loaded by an application, enable system 1300 to implement features of embodiments discussed herein. Accordingly, such computer programs represent controllers of the system 1300. Embodiments are also directed to computer program products comprising software stored on any computer useable medium. Such software, when executed in one or more data processing devices, causes a data processing device(s) to operate as described herein. Embodiments may employ any computer-useable or computer-readable medium, known now or in the future. Examples of computer-readable mediums include, but are not limited to memory devices and storage structures such as RAM, hard drives, floppy disks, CD ROMs, DVD ROMs, zip disks, tapes, magnetic storage devices, optical storage devices, MEMs, nanotechnology-based storage devices, and the like.

In alternative implementations, system 1300 may be implemented as hardware logic/electrical circuitry or firmware. In accordance with further embodiments, one or more of these components may be implemented in a system-on-chip (SoC). The SoC may include an integrated circuit chip that includes one or more of a processor (e.g., a microcontroller, microprocessor, digital signal processor (DSP), etc.), memory, one or more communication interfaces, and/or further circuits and/or embedded firmware to perform its functions.

III. Additional Example Embodiments

A method for calibrating a display device is described herein. The method includes: obtaining first information about a user of the display device, the first information comprising at least one of visual acuity information or pupillary information of the user; determining second information about the user of the display device, the second information comprising demographic information of the user; determining a value of a display parameter of the display device based on at least the first information and the second information; and providing the determined value of the display parameter for application to the display device.

In one embodiment of the foregoing method, the display parameter comprises at least one of a screen contrast, a screen brightness, a screen resolution, a font size, a font effect or a font orientation.

In another embodiment of the foregoing method, the visual acuity information is obtained by presenting a visual acuity test to the user and ascertaining visual acuity information of the user based on user input concerning the visual acuity test.

In yet another embodiment of the foregoing method, the visual acuity information is obtained by presenting a visual acuity test to the user and obtaining a pupil dilation measurement of the user in response to the presentation of the visual acuity test.

In still another embodiment of the foregoing method, the pupillary information is obtained based at least on an image of an eye of the user captured by an eye tracking device.

In yet another embodiment of the foregoing method, the demographic information comprises at least one of an age, a gender, an ethnicity, a location, a vision correction requirement, or a reading comprehension level for the user.

In still another embodiment of the foregoing method, the determining second information about the user of the display device comprises determining the second information from at least one of a user input, a user profile, display device information, or data captured by the display device.

In yet another embodiment of the foregoing method, the display device comprises one of a display screen, a projector, a virtual-reality headset, or an augmented reality headset.

In still another embodiment of the foregoing method, the determining a value of a display parameter of the display device based on at least the first information and the second information comprises determining the value of a display parameter of the display device based on the first information, the second information and third information, the third information comprising at least one of user input, display device specific information, user environment information, displayed content information, or application context information.

In an embodiment, the foregoing method further comprises applying the determined value of the display parameter to the display device.

Another method is also described herein. The method includes: obtaining a plurality of features, wherein one of the plurality of features comprises visual acuity information or pupillary information for a user of a display device; providing the plurality of features as inputs to a model obtained through machine learning that determines a value of a display parameter of the display device based on the plurality of features; and providing the determined value of the display parameter for application to the display device.

In an embodiment of the foregoing method, the plurality of features further comprises: user input; demographic information for the user; display device specific information; user environment information; displayed content information; and application context information.

In an embodiment, the foregoing method further comprises providing an indication of the user's acceptance or rejection of the value of the determined value of the display parameter as training data to a machine learner to update the model.

In one embodiment of the foregoing method, the display parameter comprises at least one of a screen contrast, a screen brightness, a screen resolution, a font size, a font effect or a font orientation.

In another embodiment of the foregoing method, the visual acuity information is obtained by presenting a visual acuity test to the user and obtaining a pupil dilation measurement of the user in response to the presentation of the visual acuity test.

In yet another embodiment of the foregoing method, the pupillary information is obtained based at least on an image of an eye of the user captured by an eye tracking device.

In still another embodiment of the foregoing method, display device comprises one of a display screen, a projector, a virtual-reality headset, or an augmented-reality headset.

In an embodiment, the foregoing method further comprises applying the determined value of the display parameter to the display device.

A self-calibrating display system is described herein. The system includes an eye-sensing device; a display device; one or more processing circuits; one or more memory devices connected to the one or more processing circuits, the one or more memory devices storing computer program logic that are executable by the one or more processing circuits, the computer program logic comprising: calibration logic that is configured to calibrate the display device by obtaining first information about a user of the display device, the first information comprising at least one of a visual acuity information or pupillary information of the user, the first information being at least partially obtained from the eye-sensing device; determining second information about the user of the display system, the second information comprising demographic information of the user; and determining a value of a display parameter of the display device based on at least the first information and the second information; and display management logic that is configured to apply the determined value of the display parameter to the display device.

In another embodiment of the foregoing system, the display device comprises one of a display screen, a projector, a virtual-reality headset, or an augmented-reality headset.

IV. Conclusion

While various embodiments have been described above, it should be understood that they have been presented by way of example only, and not limitation. It will be understood by those skilled in the relevant art(s) that various changes in form and details may be made therein without departing from the spirit and scope of the embodiments as defined in the appended claims. Accordingly, the breadth and scope of the disclosed subject matter should not be limited by any of the above-described exemplary embodiments, but should be defined only in accordance with the following claims and their equivalents.

What is claimed is:

1. A method for calibrating a display device comprising:
    obtaining first information about a user of the display device, the first information comprising at least one of visual acuity information or pupillary information of the user;
    determining second information, the second information comprising displayed content information comprising a particular image that, when viewed by the user, caused a detectable change in a pupil size of the user;
    determining a value of a display parameter of the display device based on at least the first information and the second information; and
    providing the determined value of the display parameter for application to the display device.

2. The method of claim 1, wherein the display parameter comprises at least one of a screen contrast, a screen brightness, a screen resolution, a font size, a font effect or a font orientation.

3. The method of claim 1, wherein the visual acuity information is obtained by presenting a visual acuity test to the user and ascertaining visual acuity information of the user based on user input concerning the visual acuity test.

4. The method of claim 1, wherein the visual acuity information is obtained by presenting a visual acuity test to the user and obtaining a pupil dilation measurement of the user in response to the presentation of the visual acuity test.

5. The method of claim 1, wherein the pupillary information is obtained based at least on an image of an eye of the user captured by an eye tracking device.

6. The method of claim 1, wherein the second information further comprises demographic information, and wherein the demographic information comprises at least one of an age, a gender, an ethnicity, a location, a vision correction requirement, or a reading comprehension level for the user.

7. The method of claim 6, wherein the determining second information about the user of the display device comprises determining the second information from at least one of a user input, a user profile, display device information, or data captured by the display device.

8. The method of claim 1, wherein the display device comprises one of a display screen, a projector, a virtual-reality headset, or an augmented-reality headset.

9. The method of claim 1, wherein the determining a value of a display parameter of the display device based on at least the first information and the second information comprises:
    determining the value of a display parameter of the display device based on the first information, the second information and third information, the third information comprising user input.

10. The method of claim 1, further comprising:
    applying the determined value of the display parameter to the display device.

11. The method of claim 1, wherein the particular image is intended to provoke an emotional response from the user.

12. A method, comprising:
    obtaining a plurality of features, wherein the plurality of features comprises visual acuity information or pupillary information for a user of a display device and displayed content information comprising a particular image that, when viewed by the user, caused a detectable change in a pupil size of the user;
    providing the plurality of features as inputs to a model obtained through machine learning that determines a value of a display parameter of the display device based on the plurality of features; and
    providing the determined value of the display parameter for application to the display device.

13. The method of claim 12, wherein the plurality of features further comprises:
    user input.

14. The method of claim 12, further comprising:
    providing an indication of the user's acceptance or rejection of the value of the determined value of the display parameter as training data to a machine learner to update the model.

15. The method of claim 12, wherein the display parameter comprises at least one of a screen contrast, a screen brightness, a screen resolution, a font size, a font effect or a font orientation.

16. The method of claim 12, wherein the visual acuity information is obtained by presenting a visual acuity test to the user and obtaining a pupil dilation measurement of the user in response to the presentation of the visual acuity test.

17. The method of claim 12, wherein the pupillary information is obtained based at least on an image of an eye of the user captured by an eye tracking device.

18. The method of claim 12, wherein the display device comprises one of a display screen, a projector, a virtual-reality headset, or an augmented-reality headset.

19. The method of claim 12, further comprising:
    applying the determined value of the display parameter to the display device.

20. The method of claim 12, wherein the particular image is intended to provoke an emotional response from the user.

21. A self-calibrating display system, comprising:
    an eye-sensing device;
    a display device;
    one or more processing circuits;
    one or more memory devices connected to the one or more processing circuits, the one or more memory devices storing computer program logic that are executable by the one or more processing circuits, the computer program logic comprising:
        calibration logic that is configured to calibrate the display device by:
            obtaining first information about a user of the display device, the first information comprising at least one of a visual acuity information or pupillary information of the user, the first information being at least partially obtained from the eye-sensing device;
            determining second information, the second information comprising displayed content information comprising a particular image that, when viewed by the user, caused a detectable change in a pupil size of the user;
            determining a value of a display parameter of the display device based on at least the first information and the second information; and display management logic that is configured to apply the determined value of the display parameter to the display device.

22. The system of claim 21, wherein the particular image is intended to provoke an emotional response from the user.

* * * * *